(12) United States Patent
Cho et al.

(10) Patent No.: US 7,722,926 B2
(45) Date of Patent: May 25, 2010

(54) ORGANOMETALLIC COMPOUNDS AND METHODS OF FORMING THIN FILMS INCLUDING THE USE OF THE SAME

(75) Inventors: Kyu-Ho Cho, Seongnam-si (KR); Seung-Ho Yoo, Daejeon (KR); Byung-Soo Kim, Daejeon (KR); Jae-Sun Jung, Gongju-si (KR); Han-Jin Lim, Seoul (KR); Ki-Chul Kim, Seongnam-si (KR); Jae-Soon Lim, Seoul (KR)

(73) Assignees: Samsung Electronics Co., Ltd. (KR); Techno Semichem Co., Ltd. (KR)

( * ) Notice: Subject to any disclaimer, the term of this patent is extended or adjusted under 35 U.S.C. 154(b) by 700 days.

(21) Appl. No.: 11/460,485

(22) Filed: Jul. 27, 2006

(65) Prior Publication Data

US 2007/0031597 A1    Feb. 8, 2007

(30) Foreign Application Priority Data

Aug. 2, 2005    (KR) ............... 10-2005-0070798

(51) Int. Cl.
 *C23C 16/00* (2006.01)
(52) U.S. Cl. .................. 427/255.28; 427/255.23; 568/412
(58) Field of Classification Search .......... 427/399, 427/255.28, 255.23; 568/412
See application file for complete search history.

(56) References Cited

U.S. PATENT DOCUMENTS 6,485,784 B1    11/2002    Leedham et al.
2003/0008072 A1*    1/2003    Lee et al. ............ 427/255.28
2003/0124251 A1*    7/2003    Onozawa et al. ....... 427/255.28

FOREIGN PATENT DOCUMENTS

| EP | 1 184 485 A1 | 6/2002 |
|---|---|---|
| EP | 1 433 874 A2 | 6/2004 |
| JP | 2002-114833 | 4/2002 |
| KR | 2001-78759 | 8/2001 |

OTHER PUBLICATIONS

Lee et al. ("Chemical vapor deposition of barium strontium titanate films using a single mixture of metalorganic precursors" J. Vac. Sci. Technol. A 17 (5) Sep./Oct. 1999 pp. 3115-3117).*

* cited by examiner

*Primary Examiner*—Michael Barr
*Assistant Examiner*—Robert S Walters, Jr.
(74) *Attorney, Agent, or Firm*—Myers Bigel Sibley & Sajovec, PA

(57) ABSTRACT

The present invention provides organometallic compounds and methods of forming thin films including using the same. The organometallic compounds include a metal and a ligand linked to the metal. The ligand can be represented by the following formula (1):

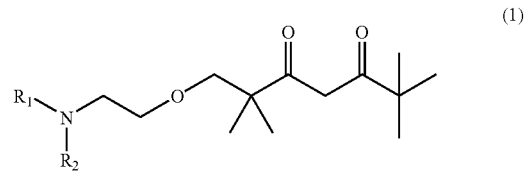

(1)

wherein $R_1$ and $R_2$ are each independently hydrogen or an alkyl group. The thin films may be applied to semiconductor structures such as a gate insulation layer of a gate structure and a dielectric layer of a capacitor.

19 Claims, 11 Drawing Sheets

ORGANOMETALLIC COMPOUNDS AND METHODS OF FORMING THIN FILMS INCLUDING THE USE OF THE SAME

CROSS-REFERENCE TO RELATED APPLICATION

This application claims priority from Korean Patent Application No. 2005-0070798, filed Aug. 2, 2005, the disclosure of which is hereby incorporated by reference in its entirety.

FIELD OF THE INVENTION

Embodiments of the present invention relates to organometallic compounds and methods of forming thin films including the use of the same. More particularly, embodiments of the present invention relate to organometallic compound having a novel ligand and methods of forming thin films including the use of the same.

BACKGROUND OF THE INVENTION

Materials having a high dielectric constant may be used for forming a thin film in a semiconductor device such as a gate insulation layer of a metal oxide semiconductor (MOS) transistor, a dielectric layer of a capacitor or a dielectric layer of a flash memory device. The thin film including a high-dielectric (k) material may possess a thin equivalent oxide thickness (EOT) and may reduce the leakage current between a gate electrode and a channel, or between a lower electrode and an upper electrode. The thin film may also improve the coupling ratio of the flash memory device.

Examples of a high-k material include tantalum oxide ($Ta_2O_5$), yttrium oxide ($Y_2O_3$), hafnium oxide ($HfO_2$), zirconium oxide ($ZrO_2$), niobium oxide ($Nb_2O_5$), barium titanium oxide ($BaTiO_3$), strontium titanium oxide ($SrTiO_3$), etc.

A thin film including strontium titanium oxide ($SrTiO_3$) may be formed using a strontium compound, a titanium compound as an organometallic compound and an oxidizing agent. A thin film including strontium ruthenium oxide ($SrRuO_3$) may be formed using a strontium compound, a ruthenium compound as an organometallic compound and an oxidizing agent.

Examples of the strontium compound for forming the thin film including strontium titanium oxide or strontium ruthenium oxide may include strontium tetramethyl heptadione ($Sr(TMHD)_2$) or strontium methylethoxy tetramethyl heptadione ($Sr(METHD)_2$). Methylethoxy tetramethyl heptadione may serve as ligands for the organometallic compound.

A strontium oxide layer formed using $Sr(TMHD)_2$ or $Sr(METHD)_2$ may have a high dielectric constant. However, $Sr(TMHD)_2$ or $Sr(METHD)_2$ may be vaporized in a canister having a temperature of higher than about 250° C. In order to form the strontium oxide layer at a temperature of lower than about 250° C., considerable time may be involved to provide $Sr(TMHD)_2$ or $Sr(METHD)_2$ into a chamber. As the amount of time increases, throughput in the manufacturing process of semiconductor devices may decrease. Additionally, it may be beneficial to provide a method of forming a metal oxide layer having a high dielectric constant and a good step coverage using a material with suitable volatility.

SUMMARY OF THE INVENTION

Embodiments of the present invention provide an organometallic compound having improved characteristics.

Embodiments of the present invention provide an organometallic compound including a metal and a ligand linked to the metal, the ligand having the following formula (1):

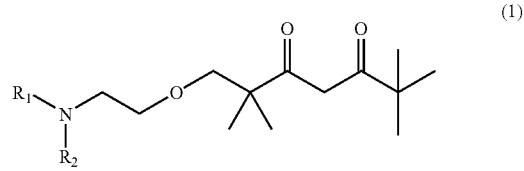

wherein $R_1$ and $R_2$ are each independently hydrogen or an alkyl group. In some embodiments, the alkyl group is a $C_1$ to $C_5$ alkyl group. In some embodiments, the ligand includes dimethylamino ethoxy tetramethyl heptadione. In still other embodiments, the organometallic compound has the following formula (2):

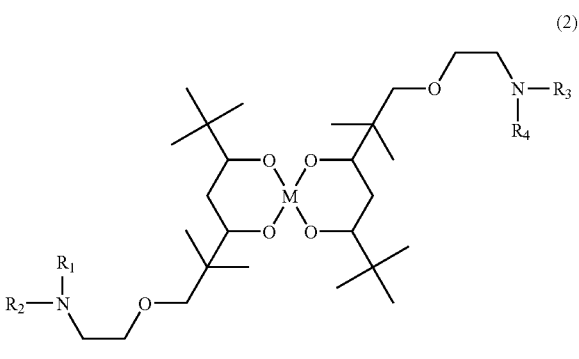

wherein $R_1$, $R_2$, $R_3$ and $R_4$ are each independently hydrogen or an alkyl group, and M is a Group IIA metal.

Embodiments of the present invention further provide methods of forming a thin film including introducing an oxidizing agent and a reactant including a first organometallic compound and a second organometallic compound onto a substrate, the first organometallic compound including a ligand having the following formula (1):

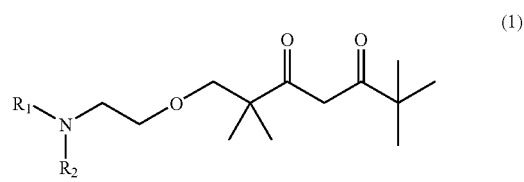

wherein $R_1$ and $R_2$ are each independently hydrogen or an alkyl group; and forming a solid material including a first metal oxide and a second metal oxide on the substrate by reacting the oxidizing agent and the reactant. In some embodiments, forming the solid material includes introducing the reactant onto the substrate, chemisorbing a first portion of the reactant on the substrate and physisorbing a second portion of the reactant on the substrate, introducing the oxidizing agent onto the substrate and reacting the first portion of the reactant with the oxidizing agent. In some embodiments, the method further includes removing the second portion of the reactant and removing the portion of the oxidizing agent that has not reacted with the first portion of the reactant.

According to embodiments of the present invention, when a thin film including a metal oxide such as a strontium titanium oxide or a strontium ruthenium oxide is formed using an organometallic compound as provided herein, the organometallic compound may have improved volatility and reactivity with an oxidizing agent. Thus, during the manufacturing process of a semiconductor device, the throughput of the semiconductor device may be improved. Additionally, a thin film formed using an organometallic compound provided herein may have a high dielectric constant and a decreased leakage current.

BRIEF DESCRIPTION OF THE DRAWINGS

The above and other features and aspects of the present invention will become more apparent by describing in detail embodiments thereof with reference to the accompanying drawings, in which.

DETAILED DESCRIPTION

Figure 1:
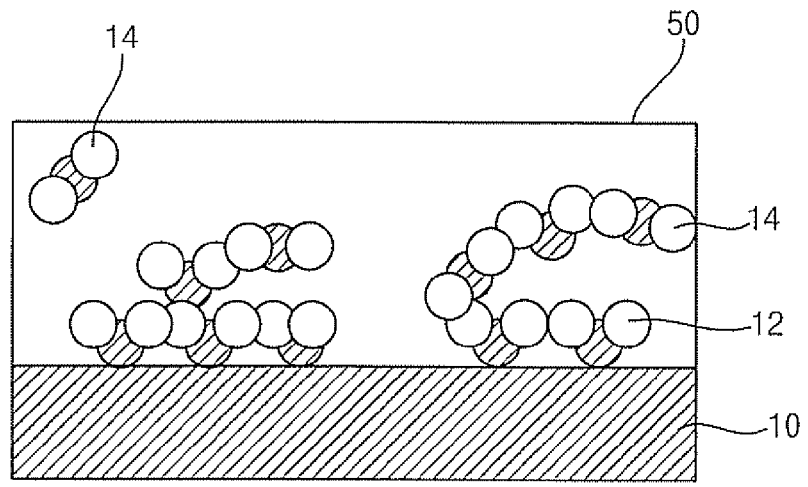
FIGS. 1 to 5 present cross-sectional views illustrating a method of forming a thin film in accordance with some embodiments of the present invention.

The present invention will now be described more fully hereinafter with reference to the accompanying drawings, in which embodiments of the present invention are shown. The present invention may, however, be embodied in many different forms and should not be construed as being limited to the embodiments set forth herein. Rather, these embodiments are provided so that this disclosure will be thorough and complete, and will fully convey the scope of the present invention to those skilled in the art.

The terminology used in the description of the present invention herein is for the purpose of describing particular embodiments only and is not intended to be limiting of the present invention. As used in the description of the embodiments of the present invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms, including technical and scientific terms used in this description, have the same meaning as commonly understood by one of ordinary skill in the art to which the present invention belongs. All publications, patent applications, patents, and other references mentioned herein are incorporated by reference in their entirety.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Moreover, it will be understood that steps comprising the methods provided herein can be performed independently or at least two steps can be combined. Additionally, steps comprising the methods provided herein, when performed independently or combined, can be performed at the same temperature and/or atmospheric pressure or at different temperatures and/or atmospheric pressures without departing from the teachings of the present invention.

In the drawings, the thickness of layers and regions are exaggerated for clarity. It will also be understood that when a layer is referred to as being "on" another layer or substrate or a reactant is referred to as being introduced, exposed or feed "onto" another layer or substrate, it can be directly on the other layer or substrate, or intervening layers can also be present. However, when a layer, region or reactant is described as being "directly on" or introduced, exposed or feed "directly onto" another layer or region, no intervening layers or regions are present. Additionally, like numbers refer to like compositions or elements throughout.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments of the present invention are further described herein with reference to cross-section illustrations that are schematic illustrations of idealized embodiments of the present invention. As such, variations from the shapes of the illustrations as a result, for example, of manufacturing techniques and/or tolerances, are to be expected. In particular, the regions illustrated in the figures are schematic in nature and their shapes are not intended to illustrate the precise shape of a region of a device and are not intended to limit the scope of the present invention.

As will be appreciated by one of ordinary skill in the art, the present invention may be embodied as compositions and devices including the compositions as well as methods of making and using such compositions and devices.

Organometallic Compound

An organometallic compound according to embodiments of the present invention includes a metal and a ligand linked to the metal. The organometallic compound may be applied to form a thin film having a high dielectric constant of more than about 100. In addition, the organometallic compound may have a suitable volatility.

The organometallic compound includes a ligand represented by the following formula (1):

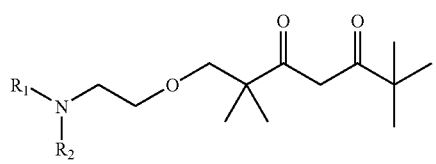

(1)

wherein $R_1$ and $R_2$ are each independently hydrogen or an alkyl group. In some embodiments, the alkyl group is a $C_1$ to $C_5$ alkyl group. In some embodiments, the ligand is dimethylamino ethoxy tetramethyl heptadione.

The organometallic compound includes the metal and the ligand linked to the metal and terminated with an amine group. In some embodiments, the metal is a Group IIA metal. Examples of suitable metals may include, but are not limited to, strontium (Sr), barium (Ba), calcium (Ca), magnesium (Mg), beryllium (Be), etc. In some embodiments, the metal is strontium.

According to some embodiments of the present invention the organometallic compound is represented by the following formula (2):

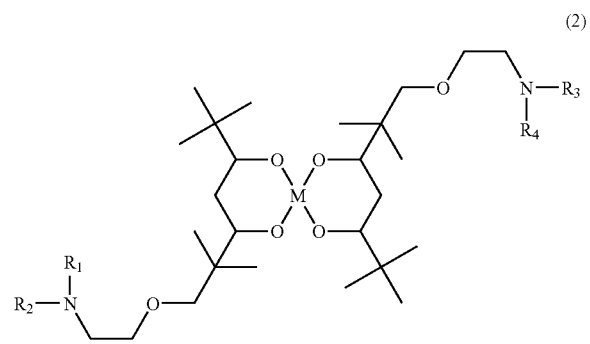

(2)

wherein $R_1$, $R_2$, $R_3$ and $R_4$ are each independently hydrogen or an alkyl group, and M is a metal such as strontium, barium, calcium, magnesium or beryllium. In some embodiments, the alkyl group is a $C_1$ to $C_5$ alkyl group. In other embodiments of the present invention, the metal is strontium, and $R_1$, $R_2$, $R_3$ and $R_4$ are hydrogen.

The organometallic compound represented by formula (2) may have an improved volatility compared to a conventional organometallic compound.

Preparation of the Organometallic Compounds

An organometallic compound according to various embodiments of the present invention can be prepared as described herein.

A flask was prepared in an ice bath. About 53.32 g 2,2-dimethyl propionyl chloride having a structure of formula (4) (shown below) was diluted in about 100 ml toluene in the flask. 32 g 2-dimethylamino ethanol having a structure of formula (3) (shown below) was slowly added dropwise into the flask. A solution of potassium hydroxide (KOH) was dropped into the flask to neutralize the above solution. Then, a toluene layer and a water layer were separated and the remaining water in the toluene layer was removed from the toluene layer. After toluene removal, decompression purification was performed. Thus, 3-chloro-2,2-dimethyl propionic acid 2-dimethylamino ethyl ester having a structure of formula (5) (shown below) was obtained. The yield of 3-chloro-2,2-dimethyl propionic acid 2-dimethylamino ethyl ester was about 70%. The reaction described above was performed at a temperature of about 0° C. The formulas described above are presented below:

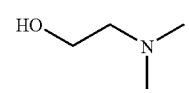

(3)

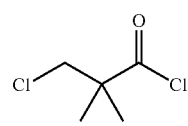

(4)

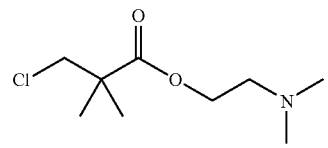

(5)

Subsequently, sodium and 2-dimethylamino ethanolamine were introduced into a flask in an ice bath to obtain a sodium salt having a structure of formula (6) (shown below). About 50 ml 1,3-dimethyl-2-imidazolidinone (DMI) was introduced into the flask. Thereafter, 3-chloro-2,2-dimethyl propionic acid 2-dimethylamino ethyl ester having a structure of formula (5) (shown above) was diluted in about 100 ml DMI. About 50 ml sodium salt diluted with DMI was introduced into the 3-chloro-2,2-dimethyl-propionic acid 2-dimethylamino ethyl ester diluted with DMI. A reflex reaction was performed to generate sodium chloride. A resultant including sodium chloride was filtered and purified in a decompression condition. Consequently, 3-(2-dimethylamino-ethyl ethoxy)-2,2-dimethyl propionic acid 2-dimethylamino ethyl ester having a structure of formula (7) (shown below) was obtained. The formulas described above are presented below:

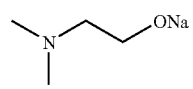

(6)

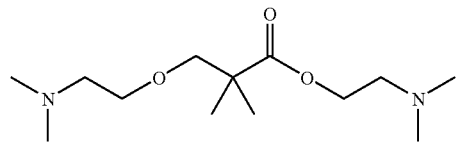

(7)

About 4.73 g $NaNH_2$ and about 80 ml anhydride toluene were introduced into a 250 ml volumetric branched flask for mixing. About 12 ml pinacolone was introduced into the flask in an ice bath. Thus, sodium pinacolone salt having the structure according to formula (8) (shown below) was obtained. About 15 g 3-(2-dimethylamino-ethyl ethoxy)-2,2-dimethyl propionic acid 2-dimethylamino ethyl ester was dissolved in about 50 ml toluene. Toluene including 3-(2-dimethylaminoethyl ethoxy)-2,2-dimethyl propionic acid 2-dimethylamino ethyl ester was introduced into the flask. A reflex reaction was performed at a temperature of about 60° C. for about 6 hours. Hydrochloric acid was introduced to provide a weak acidic condition. A resultant was cleaned with a solution of about 1.0M NaHCO$_3$/H$_2$O. A toluene layer was separated for purification in a decompression condition. Thus, 1-(2-dimethylamino ethoxy)-2,2,6,6,-tetramethyl heptane-3,5-dione having the structure of formula (9) (shown below) was obtained.

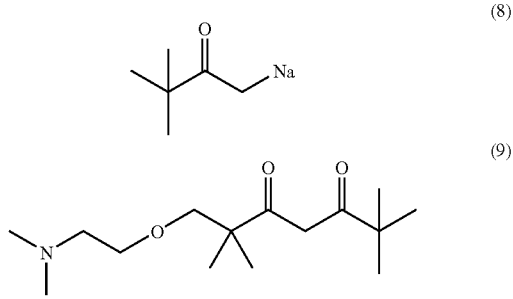

M(OEt)$_2$ and anhydride n-hexane were introduced into a flask for mixing. About 1.72 g 1-(2-dimethylamino ethoxy)-2,2,6,6,-tetramethyl heptane-3,5-dione having a structure of formula (9) (shown above) was slowly introduced into the flask. During the reaction, the ethoxy group of M(OEt)$_2$ was substituted for 1-(2-dimethylamino ethoxy)-2,1,6,6,-tetramethyl heptane-3,5-dione having the structure of formula (9) (shown above). A resultant was cooled at a temperature of about −40° C. and recrystallized. Thus, an organometallic compound according to some embodiments of the present invention having the structure of formula (2) above was obtained.

Methods of Forming a Thin Film

FIGS. 1 to 5 present cross-sectional views illustrating a method of forming a thin film according to some embodiments of the present invention.

Referring to FIG. 1, a substrate 10 may be loaded into a chamber 50. When a temperature inside the chamber 50 is lower than about 250° C., reactivity in a subsequent process may be decreased. When the temperature inside the chamber 50 is higher than about 500° C., a thin film formed on the substrate 10 may be crystallized. Thus, the temperature inside the chamber 50 may be in a range of about 250° C. to about 500° C. In some embodiments, the temperature may be in a range of about 250° C. to about 400° C. In still other embodiments, the temperature may be in a range of about 300° C. to about 350° C. For example, the temperature inside the chamber 50 may be about 300° C.

When an inner pressure of the chamber 50 is less than about 0.01 Torr, the reactivity of a reactant in a subsequent process may be decreased. When the inner pressure of the chamber 50 is greater than about 10 Torr, processes may not be readily controlled. Thus, in some embodiments, the inner pressure of the chamber 50 may be in a range of about 0.01 Torr to about 10 Torr, and in some embodiments, about 0.05 Torr to about 5 Torr. In still other embodiments, the inner pressure of the chamber 50 may be in a range of about 0.1 Torr to about 3 Torr. For example, the pressure of the chamber 50 may be about 1 Torr.

A reactant including a first organometallic compound and a second organometallic compound may be introduced into the chamber 50. According to some embodiments of the present invention, the first organometallic compound is represented by the following formula (2):

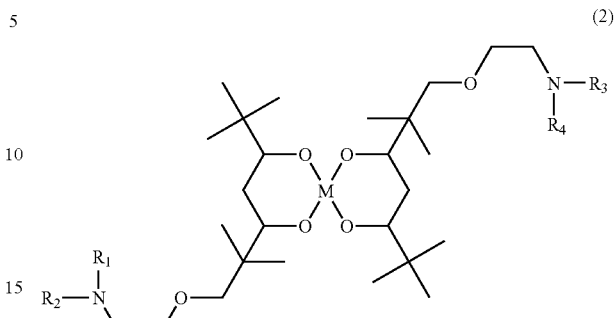

wherein R$_1$, R$_2$, R$_3$ and R$_4$ are each independently hydrogen or an alkyl group. In some embodiments, the alkyl group is C$_1$ to C$_5$ alkyl. M is a Group IIA metal. In some embodiments, M is strontium, barium, calcium, magnesium or beryllium.

According to some embodiments, the first organometallic compound includes strontium as the metal and dimethylamino ethoxy tetramethyl heptadione (DMAETHD) as a ligand, so that the first organometallic compound is Sr(DMAETHD)$_2$.

The second organometallic compound may include a titanium compound or a ruthenium compound. In some embodiments, the second organometallic compound is a titanium compound. Examples of the titanium compound may include, but are not limited to, titanium butoxide (Ti(OtBu)$_4$), tetraethylmethylamino titanium (Ti[N(CH$_3$)(C$_2$H$_5$)$_4$]), titanium ethoxide (Ti(OEt)$_4$), titanium isopropoxide (Ti(OC$_3$H$_7$)$_4$), tetramethylheptadione titanium (Ti(C$_{11}$H$_{19}$O$_2$)$_2$), etc. These titanium compounds can be used alone or in a mixture thereof.

According to some embodiments of the present invention, a ratio between the first organometallic compound and the second organometallic compound may be in a range of about 1:0.5 to about 1:5. In some embodiments, the ratio between the first organometallic compound and the second organometallic compound is about 1:1.

According to some embodiments of the present invention, the reactant including the first organometallic compound and the second organometallic compound may be introduced into the chamber 50 by a liquid delivery system (LDS). The reactant may be introduced into the chamber 50 for a period of time in a range of about 0.5 seconds to about 5 seconds. In some embodiments, the reactant is introduced into the chamber 50 for about 1 second.

According to some embodiments of the present invention, a first portion 12 of the reactant is chemisorbed onto the substrate 10. A second portion 14 of the reactant that is not chemisorbed onto the substrate 10 is physisorbed on the first portion 12 or drifted in the chamber 50.

Figure 2:
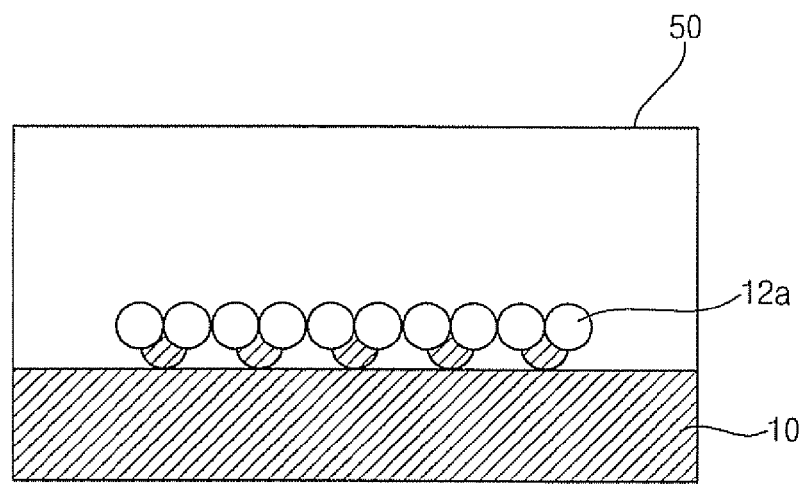

Referring to FIG. 2, a first purging gas can be introduced into the chamber 50. The first purging gas may include an inert gas such as an argon (Ar) gas or a nitrogen (N$_2$) gas. In some embodiments of the present invention, the first purging gas may be introduced into the chamber 50 for a period of time in a range from about one second to about 30 seconds. In some embodiments, the first purging gas is introduced into the chamber 50 for about 30 seconds. Some, if not all, of the second portion 14 physisorbed on the first portion 12 or drifted in the chamber 50 may be removed from the chamber 50 by introducing the first purging gas. Hence, molecules 12a, including the first portion 12, remain on the substrate 10. According to some embodiments of the present invention, the chamber 50 may be vacuumed for a period of time in a range of about one second to about 30 seconds to remove some, if not all, of the second portion 14 from the chamber 50. In still other embodiments of the present invention, both introducing the first purging gas and vacuuming the chamber 50 may be performed to remove some, if not all, of the second portion 14 from the chamber 50.

Figure 3:
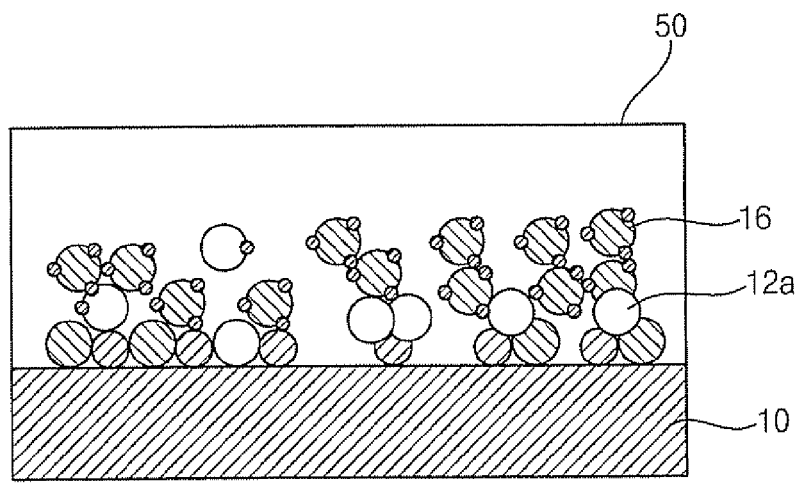

Referring to FIG. 3, an oxidizing agent 16 may be introduced into the chamber 50. Examples of the oxidizing agent 16 may include, but are not limited to, ozone ($O_3$), oxygen ($O_2$), water vapor ($H_2O$), dinitrogen oxide, dinitrogen monoxide or nitrous oxide ($N_2O$), plasma oxygen, remote plasma oxygen, etc. These can be used alone or in a mixture thereof. The oxidizing agent 16 may be introduced into the chamber 50 for a period of time in a range of about 0.5 seconds to about 5 seconds. When the oxidizing agent 16 includes ozone, contents of impurities in a metal oxide formed using the oxidizing agent 16 may be relatively decreased and the oxidizing agent may be more readily controlled. In some embodiments of the present invention, ozone may be obtained using an ozonizer such as an ozone generator. When an oxygen ($O_2$) gas is treated using the ozonizer, the oxygen gas may be partially transformed into ozone.

According to some embodiments, the oxidizing agent 16 introduced into the chamber 50 may be chemically reacted with the molecules 12a to oxidize the molecules 12a.

Figure 4:
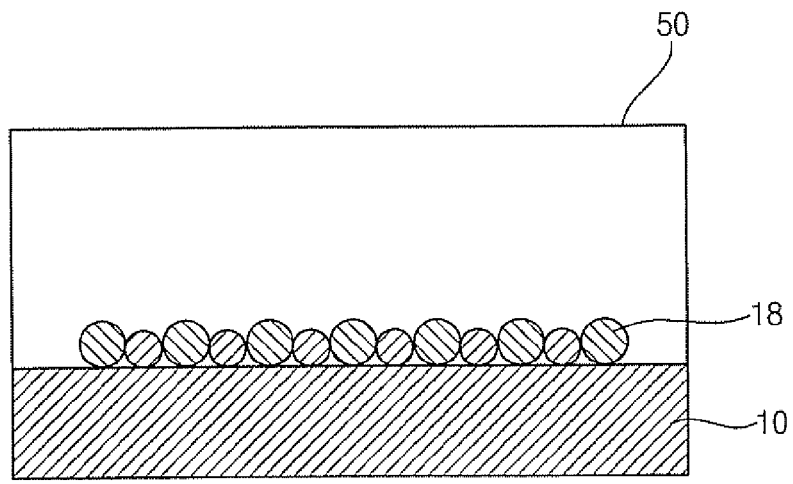

Referring to FIG. 4, a second purging gas may be introduced into the chamber 50. The second purging gas may include an inert gas such as an argon (Ar) gas or a nitrogen ($N_2$) gas. In some embodiments of the present invention, the second purging gas may be introduced into the chamber 50 for a period of time in a range of about one second to about 30 seconds. In some embodiments, the second purging gas is introduced into the chamber 50 for about 30 seconds.

The second purging gas may remove from the chamber 50 some, if not all, of the oxidizing agent 16 that is not chemically reacted with the molecules 12a. As a result, a solid material 18 including a metal oxide may be formed on the substrate 10. The metal oxide may include strontium titanium oxide. Additionally, the metal oxide may have a high dielectric constant.

Figure 5:
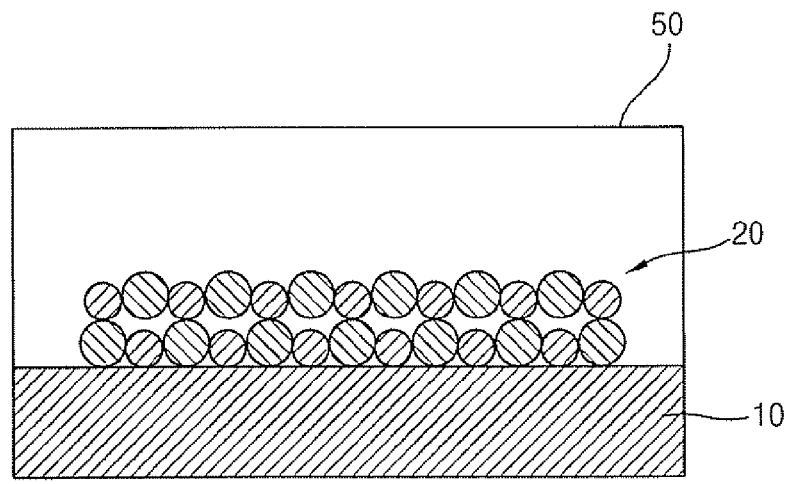

Referring to FIG. 5, the above-described steps of introducing the reactant, purging the non-chemisorbed second portion 14, introducing the oxidizing agent 16 and purging the oxidizing agent 16 may be repeatedly carried out. As a result, a thin film 20 including the solid material 18 may be formed on the substrate 10. The thin film 20 may include strontium titanium oxide. The thickness of the thin film 20 may be controlled according to the number of iterations of the above-described steps.

In some embodiments of the present invention, the thin film 20 including strontium titanium oxide may be formed by an atomic layer deposition (ALD) process using a strontium compound including Sr(DMAETHD)$_2$ and a titanium compound. In other embodiments of the present invention, the thin film 20 including strontium titanium oxide may be formed by a chemical vapor deposition (CVD) process. In the CVD process, a strontium compound including Sr(DMAETHD)$_2$ in a gas phase and a titanium compound as a reactant and an oxidizing agent may be simultaneously introduced onto a substrate in a chamber. The reactant and the oxidizing agent may be chemically reacted on the substrate to form strontium titanium oxide. Strontium titanium oxide may be chemisorbed on the substrate to form a solid material on the substrate. Strontium titanium oxide may be chemisorbed on the solid material to form a thin film including strontium titanium oxide. In some embodiments, the strontium titanium oxide is continuously chemisorbed on the solid material. The thickness of the thin film may be controlled according to the length of time of performing the CVD process.

Figure 6:
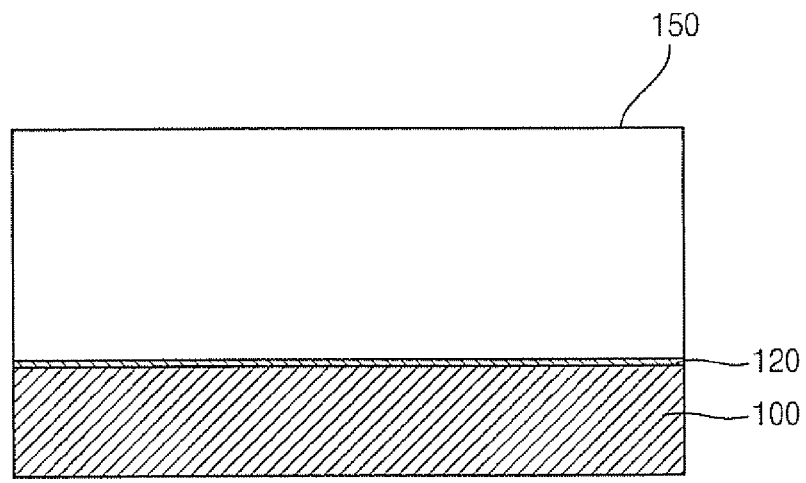
FIGS. 6 to 8 present cross-sectional views illustrating a method of forming a thin film in accordance with some embodiments of the present invention.
Figure 7:
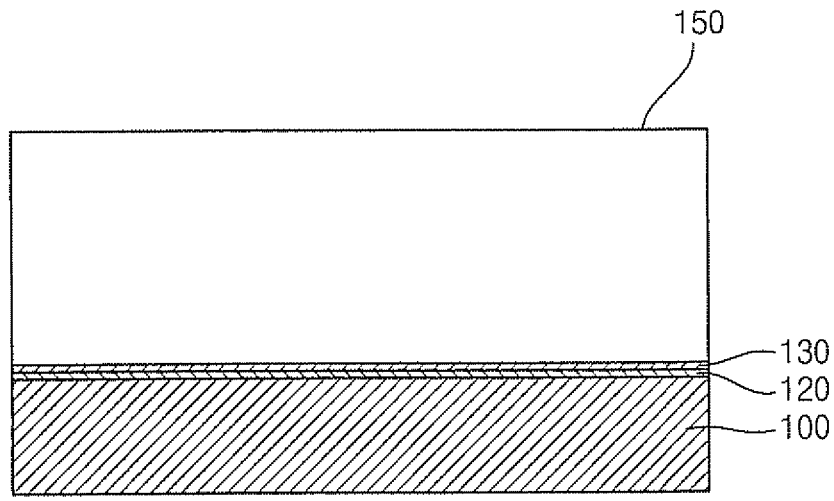
Figure 8:
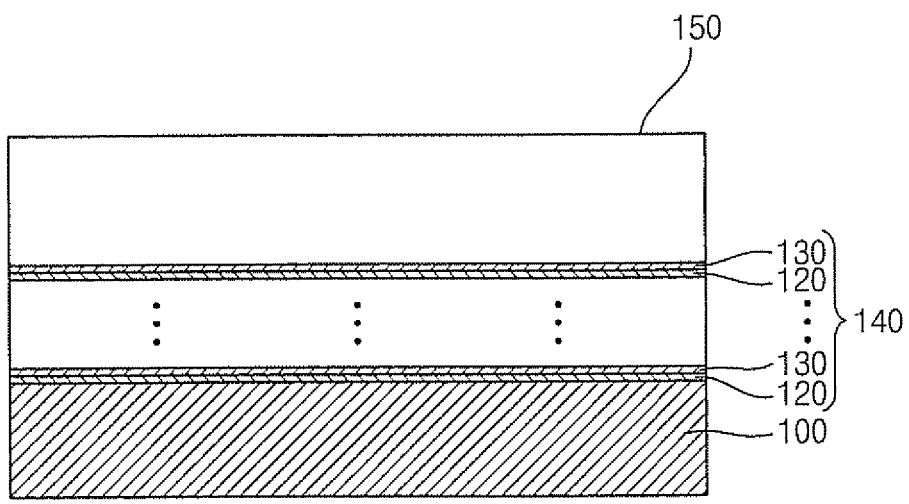

FIGS. 6 to 8 present cross-sectional views illustrating a method of forming a thin film according to some embodiments of the present invention.

Referring to FIG. 6, a substrate 100 may be loaded into a chamber 150. A first organometallic compound may be introduced onto the substrate 100. The first organometallic compound includes compounds represented by the following formula (2):

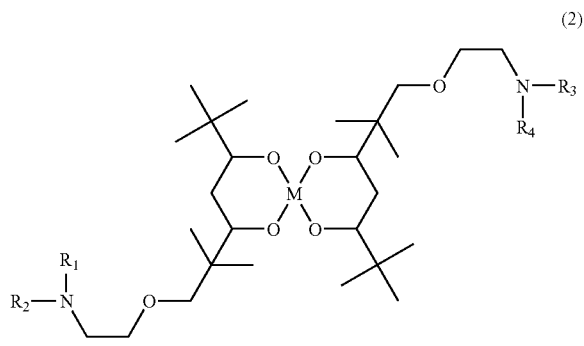

(2)

wherein $R_1$, $R_2$, $R_3$ and $R_4$ are each independently hydrogen or an alkyl group. In some embodiments, the alkyl group is $C_1$ to $C_5$ alkyl. M is a Group IIA metal. In some embodiments, M is strontium, barium, calcium, magnesium or beryllium.

In some embodiments, the first organometallic compound includes strontium as the metal and dimethylamino ethoxy tetramethyl heptadione (DMAETHD) as a ligand, so that the first organometallic compound can be Sr(DMAETHD)$_2$.

A first portion of the first organometallic compound may be chemisorbed onto the substrate 100. A second portion of the first organometallic compound may be physisorbed on the first portion or drifted in the chamber 150. A first purging gas may be introduced into the chamber 150. The first purging gas may include an inert gas such as an argon (Ar) gas or a nitrogen ($N_2$) gas. Some, if not all, of the second portion that may be physisorbed on the first portion of the first organometallic compound or drifted in the chamber 150 may be removed from the chamber 150 by introducing the first purging gas. Hence, first molecules including the first portion of the first organometallic compound may remain on the substrate 100.

A first oxidizing agent may be introduced into the chamber 150. Examples of the first oxidizing agent may include, but are not limited to, ozone ($O_3$), oxygen ($O_2$), water vapor ($H_2O$), dinitrogen oxide ($N_2O$), plasma $O_2$, remote plasma $O_2$, etc. In some embodiments, ozone may be utilized as the oxidizing agent. The first oxidizing agent introduced into the chamber 150 may be chemically reacted with the first molecules to oxidize the first molecules.

A second purging gas may be introduced into the chamber 150. The second purging gas may include an inert gas such as an argon (Ar) gas or a nitrogen ($N_2$) gas. The second purging gas may remove from the chamber 150 some, if not all, of the first oxidizing agent that is not chemically reacted with the first molecules. As a result, a first solid material 120 including a first metal oxide may be formed on the substrate 100. For example, the first solid material 120 may include strontium oxide.

Referring to FIG. 7, a second organometallic compound may be introduced onto the substrate 100 including the first solid material 120 thereon. The second organometallic compound may include a titanium compound or a ruthenium compound. For example, the second organometallic compound may include a ruthenium compound. A first portion of the second organometallic compound may be chemisorbed onto the first solid material 120 formed on the substrate 100. A second portion of the second organometallic compound may be physisorbed on the first portion or drifted in the chamber 150.

A third purging gas may be introduced into the chamber 150. The third purging gas may include an inert gas such as an argon (Ar) gas or a nitrogen ($N_2$) gas. The second portion physisorbed on the first portion of the second organometallic compound or drifted in the chamber 150 may be removed from the chamber 150 by introducing the third purging gas. As a result, second molecules including the first portion of the second organometallic compound may remain on the substrate 100.

A second oxidizing agent may be introduced into the chamber 150. Examples of the second oxidizing agent may include ozone, oxygen, water vapor, dinitrogen oxide, plasma oxygen, remote plasma oxygen, etc. The second oxidizing agent introduced into the chamber 150 may be chemically reacted with the second molecules to oxidize the second molecules.

A fourth purging gas may be introduced into the chamber 150. The fourth purging gas may include an inert gas such as an argon (Ar) gas or a nitrogen ($N_2$) gas. Some, if not all, of the second oxidizing agent that is not chemically reacted with the second molecules may be removed from the chamber 150 by introducing the fourth purging gas. As a result, a second solid material 130 including a second metal oxide is formed on the substrate 100. For example, the second solid material 130 may include ruthenium oxide.

Referring to FIG. 8, a unit process including introducing the first organometallic compound, introducing the first purging gas, introducing the first oxidizing agent, introducing the second purging gas, introducing the second organometallic compound, introducing the third purging gas, introducing the second oxidizing agent and introducing the fourth purging gas may be repeatedly carried out. As a result, a thin film 140 having a metal oxide such as strontium titanium oxide may be formed on the substrate 100. The thin film 140 may have a high dielectric constant.

Methods of Manufacturing a Gate Structure

FIGS. 9 to 12 present cross-sectional views illustrating a method of manufacturing a gate structure in accordance with some embodiments of the present invention.

Figure 9:
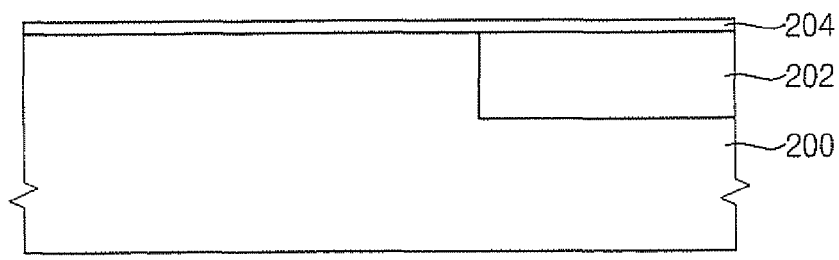
FIGS. 9 to 12 present cross-sectional views illustrating a method of manufacturing a gate structure in accordance with some embodiments of the present invention.

Referring to FIG. 9, a substrate 200 may be provided. The substrate 200 may include a silicon wafer or a silicon-on-insulator (SOI) substrate. An active region and a field region 202 may be defined on the substrate 200 by an isolation process such as a shallow trench isolation (STI) process.

A gate insulation layer 204 may be formed on the substrate 200. The gate insulation layer 204 may have a thin equivalent oxide thickness (EOT). In addition, the leakage current between a gate electrode and a channel may be sufficiently decreased by the gate insulation layer 204. Hence, the gate insulation layer 204 may include a metal oxide such as strontium titanium oxide. The gate insulation layer 204 may be formed to have a thickness in a range of about 30 Å to about 100 Å.

In some embodiments of the present invention, the gate insulation layer 204 may be formed using a strontium compound, a titanium compound and an oxidizing agent by an ALD process the same as, or similar to, the ALD process described with reference to FIGS. 1 to 5.

According to other embodiments of the present invention, the gate insulation layer 204 may be formed using a strontium compound, a titanium compound and an oxidizing agent by an ALD process the same as, or similar to, the ALD process described with reference to FIGS. 6 to 8.

In still other embodiments of the present invention, the gate insulation layer 204 may be formed by a CVD process. The CVD process may be performed by simultaneously introducing the strontium compound, the titanium compound and the oxidizing agent. In some embodiments, the strontium compound may include $Sr(DMAETHD)_2$. $Sr(DMAETHD)_2$ may have a high-saturation vapor pressure at a low temperature. Thus, $Sr(DMAETHD)_2$ may have an improved evaporability with respect to a conventional strontium compound. That is, $Sr(DMAETHD)_2$ may have a low start point and a low end point of evaporation.

In some embodiments of the present invention, a silicon oxide layer (not shown) having a thickness of about 5 Å may be further formed on the gate insulation layer 204. Subsequent thereto, the silicon oxide layer may be formed on the gate insulation layer 204 in-situ.

Figure 10:
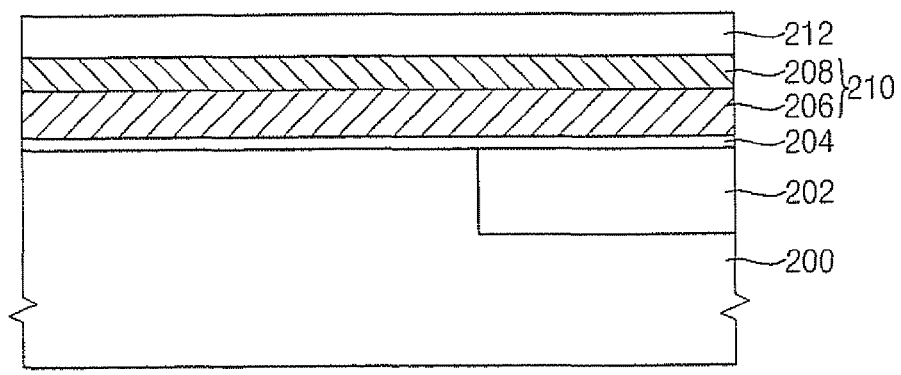

Referring to FIG. 10, a gate conductive layer 210 may be formed on the gate insulation layer 204. In some embodiments of the present invention, the gate conductive layer 210 may be formed in a multi-layered structure. For example, the gate conductive layer 210 may be formed in a multi-layered structure including a polysilicon layer 206 and a metal silicide layer 208 such as a tungsten silicide layer formed on the polysilicon layer 206. In other embodiments of the present invention, the gate conductive layer 210 may be formed in a single-layered structure.

Figure 11:
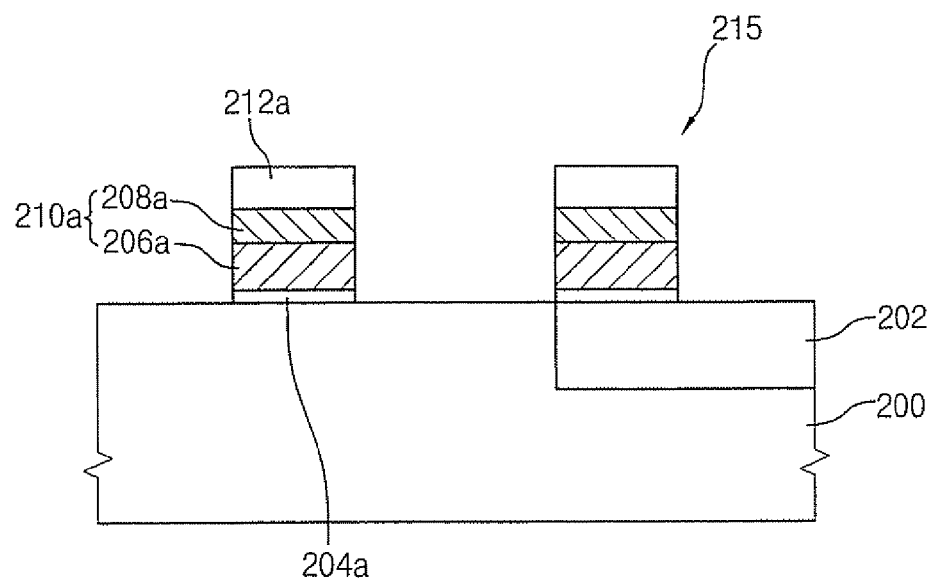

A capping layer 212 may be formed on the gate conductive layer 210 using an oxide such as silicon oxide or a nitride such as silicon nitride. Referring to FIG. 11, the capping layer 212, the gate conductive layer 210 and the gate insulation layer 204 may be successively patterned. Thus, a gate structure 215 may be formed on the substrate 200. The gate structure 215 may include a gate insulation layer pattern 204*a*, a gate conductive layer pattern 210*a* and a capping layer pattern 212*a*. The gate conductive layer pattern 210*a* may include a polysilicon layer pattern 206*a* and a metal silicide layer pattern 208*a*. The gate structure 215 may be formed using a photolithography process.

Figure 12:
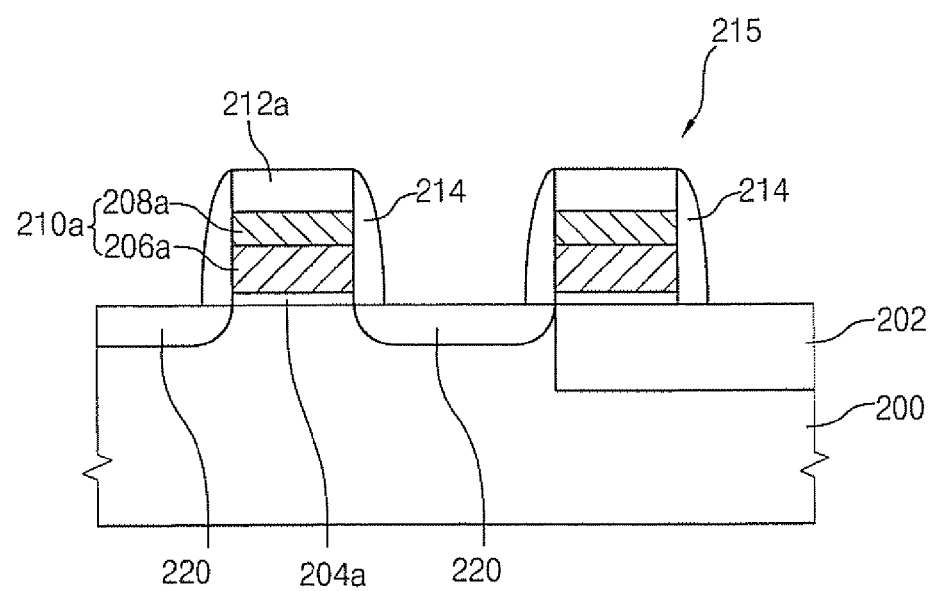

Referring to FIG. 12, source/drain regions 220 may be formed on at least some portions of the substrate 200 adjacent to the gate structure 215. A gate spacer 214 may be formed on a sidewall of the gate structure 215. In some embodiments of the present invention, the source/drain regions 220 may be formed before forming the gate insulation layer 204. In other embodiments of the present invention, the source/drain regions 220 may be formed after forming the gate spacer 214.

The gate insulation layer pattern 204*a* including strontium titanium oxide may have a thin equivalent oxide thickness (EOT). In addition, a leakage current between the gate conductive layer pattern 210*a* and the substrate 200 may be sufficiently decreased. Thus, the gate structure 215 may have improved electrical characteristics.

Methods of Manufacturing a Capacitor

Figure 13:
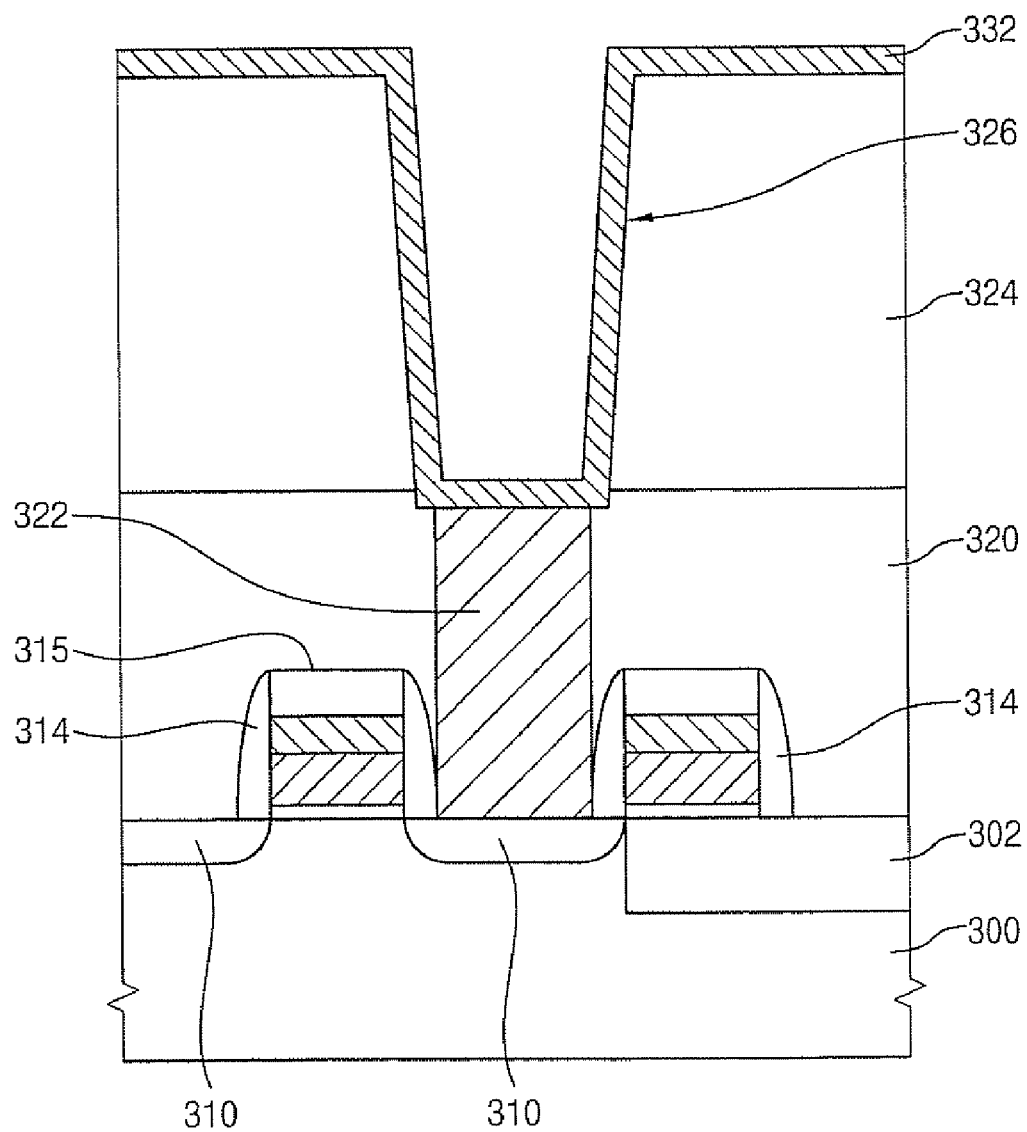
FIGS. 13 to 16 present cross-sectional views illustrating a method of manufacturing a capacitor in accordance with some embodiments of the present invention.

FIGS. 13 to 16 present cross-sectional views illustrating a method of manufacturing a capacitor according to some embodiments of the present invention. Referring to FIG. 13, an active region and a field region 302 may be defined on a substrate 300. A gate structure 315 including a gate insulation layer pattern, a conductive layer pattern and a capping layer pattern may be formed on the substrate 300. Source/drain regions 310 may be formed on portions of the substrate 300 adjacent to the gate structure 315. A gate spacer 314 may be formed on a sidewall of the gate structure 315.

An insulating interlayer 320 may be formed to cover the gate structure 315. A contact hole exposing the source/drain regions 310 may be formed in the insulating interlayer 320. A contact 322 may be formed to fill up the contact hole. The contact 322 may be formed using doped polysilicon, a metal, a conductive metal nitride, etc. The contact 322 may be electrically connected with the source/drain regions 310.

A mold layer 324 may be formed on the insulating interlayer 320 and the contact 322. In some embodiments of the present invention, before forming the mold layer 324, structures such as a plug, a pad, a bit line, an insulation layer, an etch stop layer and the like may be further formed on the insulating interlayer 320 and the contact 322.

An opening 326 exposing the contact 322 may be formed in the mold layer 324. A conductive layer 332 may be formed in the opening and on the mold layer 324. The conductive layer 332 may include doped polysilicon or a conductive metal nitride such as titanium nitride, tantalum nitride, tungsten nitride, etc., which can be used alone or in a mixture thereof.

Figure 14:
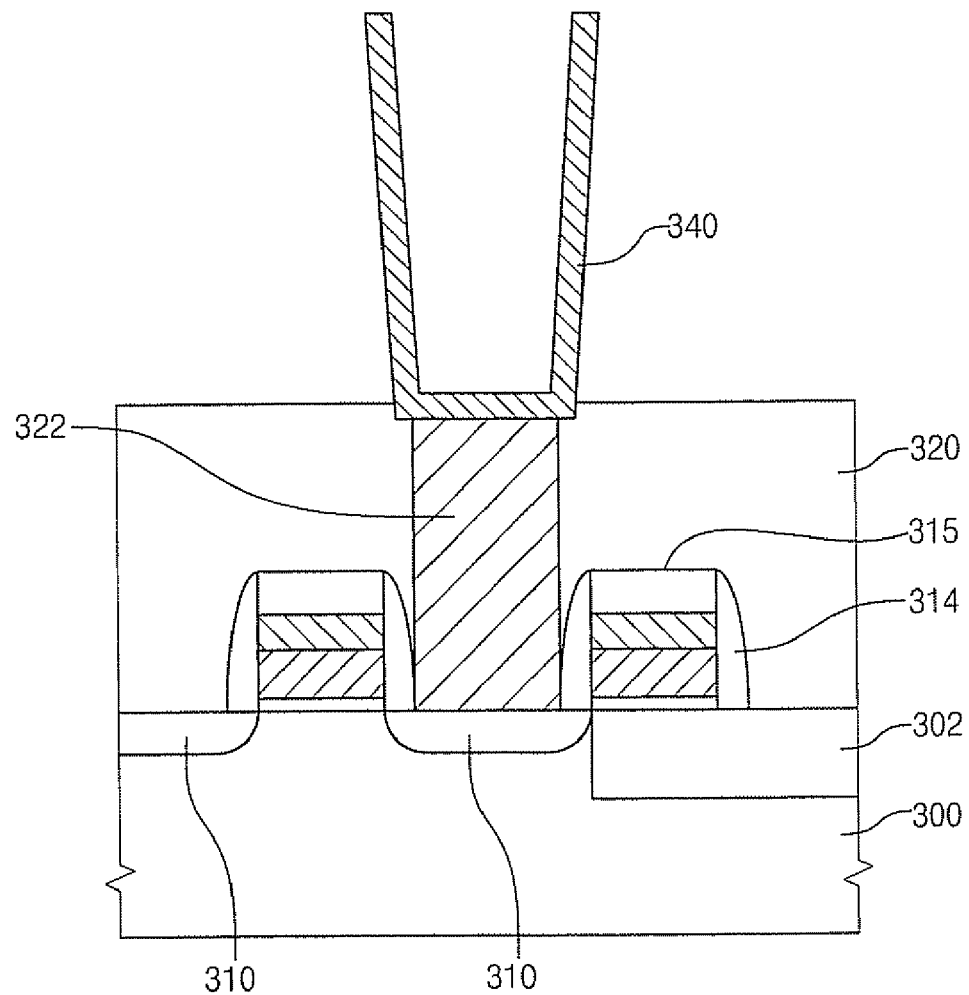

Referring to FIG. 14, a sacrificial layer may be formed on the conductive layer 332. The sacrificial layer may be removed to expose the conductive layer 332 formed on the mold layer 324. The conductive layer 332 on the mold layer 324 may be removed. The sacrificial layer may remain in the opening and the mold layer 324 may be removed to form a lower electrode 340. The lower electrode 340 may have a cylindrical shape. In some embodiments of the present invention, an upper portion of the lower electrode 340 may have a size greater than a lower portion of the lower electrode 340.

Figure 15:
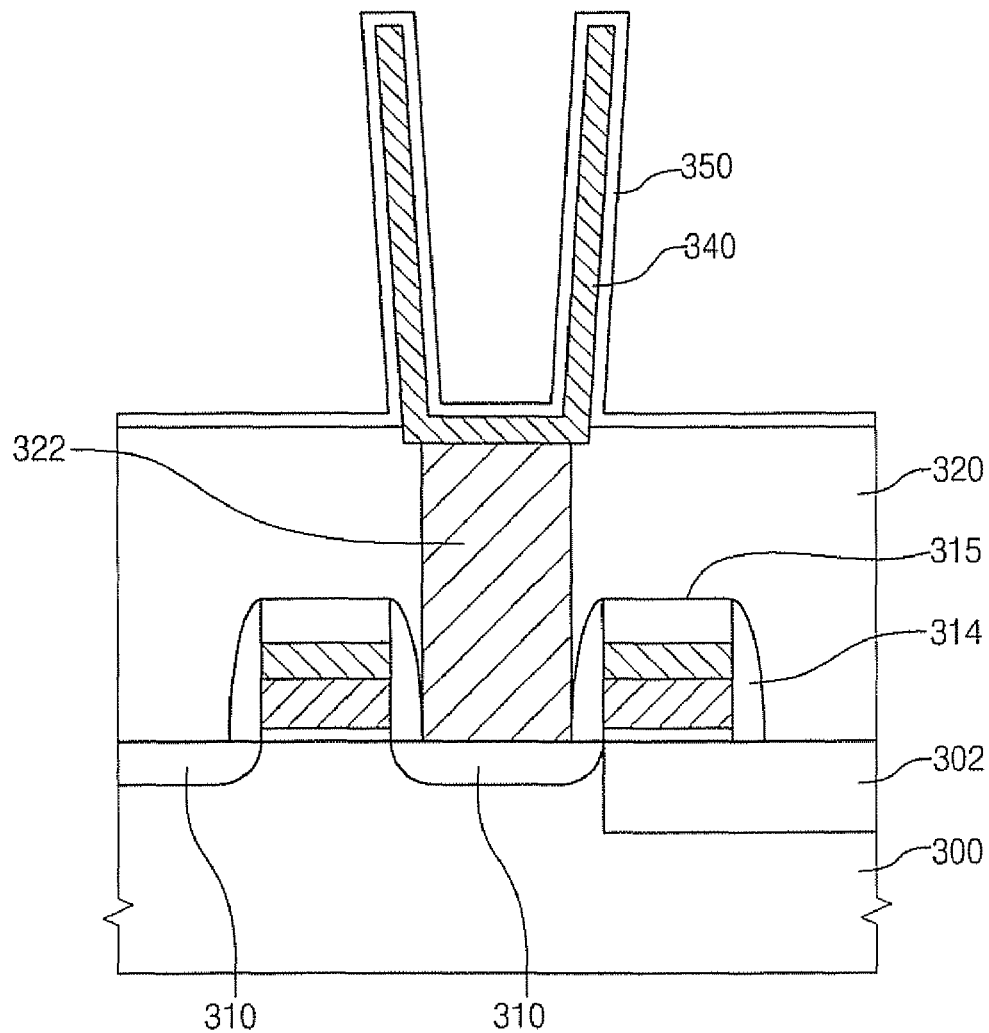

Referring to FIG. 15, a dielectric layer 350 may be formed on the lower electrode 340. The dielectric layer 350 may have a thin equivalent oxide thickness (EOT). In addition, the leakage current between a lower electrode 340 and an upper electrode may be sufficiently decreased. Hence, the dielectric layer 350 may include strontium titanium oxide. The dielectric layer 350 may be formed to have a thickness in a range of about 30 Å to about 100 Å.

In some embodiments of the present invention, the dielectric layer 350 may be formed using a strontium compound, a titanium compound and an oxidizing agent by an ALD process the same as, or similar to, the ALD process described with reference to FIGS. 1 to 5.

In other embodiments of the present invention, the dielectric layer 350 may be formed using a strontium compound, a titanium compound and an oxidizing agent by an ALD process the same as, or similar to, the ALD process described with reference to FIGS. 6 to 8.

In still further embodiments of the present invention, the dielectric layer 350 may be formed by a CVD process. The CVD process may be performed by simultaneously introducing the strontium compound, the titanium compound and the oxidizing agent.

The strontium compound may include $Sr(DMAETHD)_2$. $Sr(DMAETHD)_2$ may have a high-saturation vapor pressure at a low temperature. Thus, $Sr(DMAETHD)_2$ may have a low evaporation point with respect to a conventional strontium compound.

The dielectric layer 350 may be formed by an ALD process using the strontium compound such as $Sr(DMAETHD)_2$.

Figure 16:
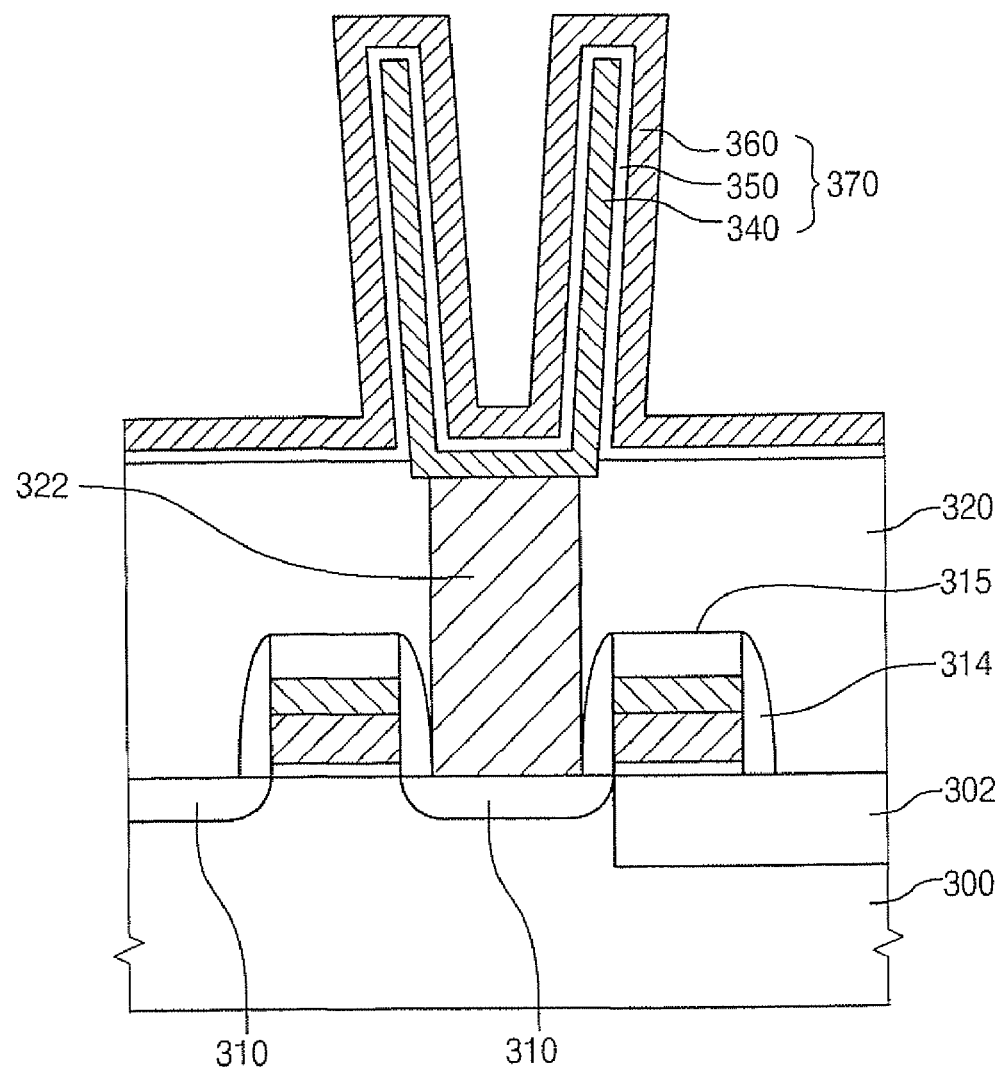

Referring to FIG. 16, a curing process may be performed on the dielectric layer 350. The curing process may serve to remove at least some of the contaminants in the dielectric layer 350 and cure the oxygen deficiency of the dielectric layer 350. The curing process may be performed by any suitable process such as an ultraviolet ozone ($UV-O_3$) treatment, a plasma treatment, a heat treatment process, etc.

An upper electrode 360 may be formed on the dielectric layer 350. The upper electrode 360 may include doped polysilicon or a conductive metal nitride such as titanium nitride, tantalum nitride, tungsten nitride, etc, which can be used alone or in a mixture thereof.

Thus, a capacitor 370 including the lower electrode 340, the dielectric layer 350 and the upper electrode 360 may be formed on the substrate 300. The dielectric layer 350 may include strontium titanium oxide having a high dielectric constant.

Measurement of Evaporability of $Sr(DMAETHD)_2$

Figure 17:
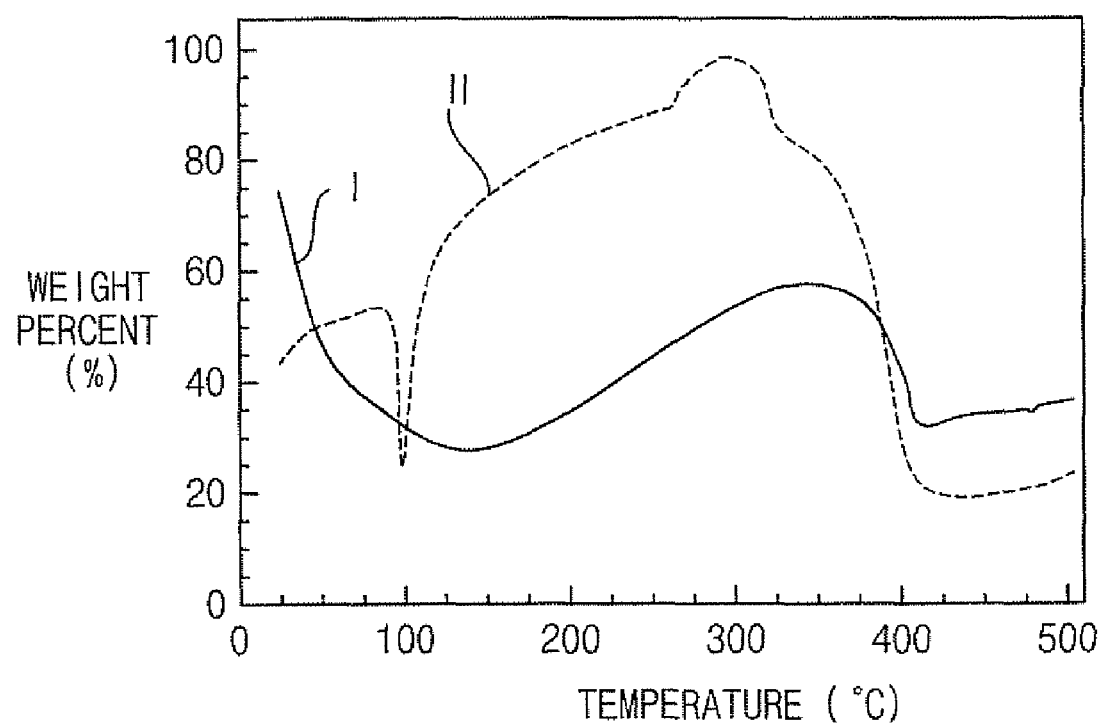
FIG. 17 presents a graph illustrating a thermogravimetric analysis (TGA) result of organic metallic compound, Sr(D-MAETHD)$_2$, according to some embodiments of the present invention and a conventional strontium compound, Sr(METHD)$_2$.

FIG. 17 presents a graph illustrating a thermogravimetric analysis (TGA) result of an organometallic compound, $Sr(DMAETHD)_2$, according to embodiments of the present invention and $Sr(METHD)_2$, which represents a conventional strontium compound.

The thermogravimetric analysis relates to a thermal analysis technique used to measure a variation of a weight of a sample relative to temperature and time. During the thermogravimetric analysis, as the temperature of the sample increases by a constant rate or is maintained isothermally, the variation of the weight of the sample due, at least in part, to thermal decomposition, sublimation, evaporation or oxidation is measured with a thermogram. In FIG. 17, I represents a thermogravimetric analysis result of organometallic compound $Sr(DMAETHD)_2$ according to embodiments of the present invention, and II represents a thermogravimetric analysis result of the conventional strontium compound $Sr(METHD)_2$.

Referring to FIG. 17, as temperatures of $Sr(DMAETHD)_2$ and $Sr(METHD)_2$, were increased by a rate of about 5° C./minute up to a temperature of about 400° C., a weight loss of $Sr(DMAETHD)_2$ and $Sr(METHD)_2$ were measured. A sudden weight loss of $Sr(DMAETHD)_2$ or $Sr(METHD)_2$ is believed to be caused by an evaporation of $Sr(DMAETHD)_2$ and $Sr(METHD)_2$, respectively. Thus, evaporation of $Sr(DMAETHD)_2$ may start at a lower temperature relative to that of $Sr(METHD)_2$. In addition, evaporation of $Sr(DMAETHD)_2$ terminates at a lower temperature relative to that of $Sr(METHD)_2$.

According to embodiments of the present invention, when a thin film including a metal oxide such as a strontium titanium oxide or a strontium ruthenium oxide is formed using an organometallic compound, the organometallic compound of the present invention may have improved volatility and reactivity. Thus, during a manufacturing process of a semiconductor device, a throughput of the semiconductor device may be improved. In addition, the thin film formed using the organometallic compound may have a high dielectric constant and a decreased leakage current. The thin film may be utilized as a gate insulation layer of a gate structure or a dielectric layer of a capacitor, etc.

The foregoing is illustrative of the present invention and is not to be construed as limiting thereof. Therefore, it is to be understood that modifications to the described embodiments, as well as other embodiments, are intended to be included within the scope of the appended claims. The present invention is defined by the following claims, with equivalents of the claims to be included therein.

What is claimed is:

1. An organometallic compound comprising:
a metal; and
a ligand linked to the metal, the ligand having the following formula (1):

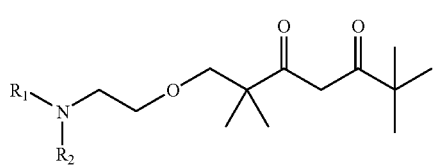

wherein $R_1$ and $R_2$ are each independently hydrogen or an alkyl group.

2. The organometallic compound of claim 1, wherein the alkyl group is a $C_1$ to $C_5$ alkyl group.

3. The organometallic compound of claim 1, wherein the ligand comprises dimethylamino ethoxy tetramethyl heptadione.

4. The organometallic compound of claim 1, wherein the metal is a Group IIA metal.

5. The organometallic compound of claim 1, wherein the organometallic compound has the following formula (2):

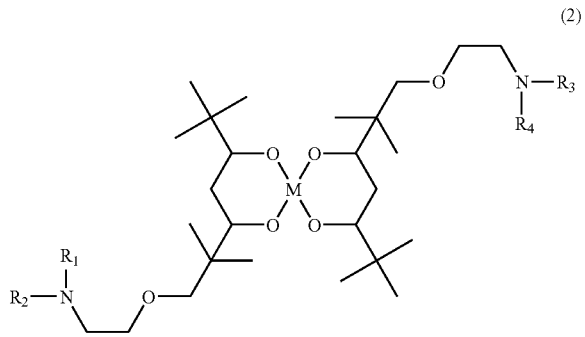

wherein $R_1$, $R_2$, $R_3$ and $R_4$ are each independently hydrogen or an alkyl group, and M is strontium (Sr), barium (Ba), calcium (Ca), magnesium (Mg) or beryllium (Be).

6. The organometallic compound of claim 5, wherein the alkyl group is a $C_1$ to $C_5$ alkyl group.

7. A method of forming a thin film comprising:
introducing an oxidizing agent and a reactant comprising a first organometallic compound and a second organometallic compound onto a substrate, the first organometallic compound comprising a ligand having the following formula (1); and

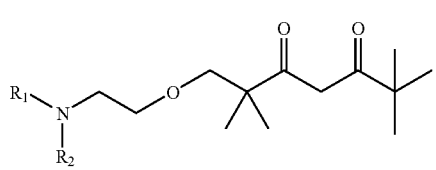

wherein $R_1$ and $R_2$ are each independently hydrogen or a $C_1$ to $C_5$ alkyl group,
forming a solid material comprising a first metal oxide and a second metal oxide on the substrate by reacting the oxidizing agent and the reactant.

8. The method of claim 7, wherein the first organometallic compound has the formula (2):

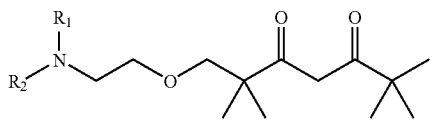

wherein $R_1$, $R_2$, $R_3$ and $R_4$ are each independently hydrogen or a $C_1$ to $C_5$ alkyl group, and M is strontium (Sr), barium (Ba), calcium (Ca), magnesium (Mg) or beryllium (Be).

9. The method of claim 7, wherein the second organometallic compound comprises a titanium compound or a ruthenium compound.

10. The method of claim 7, wherein the oxidizing agent comprises at least one oxidizing agent selected from the group consisting of ozone ($O_3$), oxygen ($O_2$), water vapor ($H_2O$), dinitrogen oxide ($N_2O$), plasma oxygen and remote plasma oxygen.

11. The method of claim 7, wherein the solid material is a gate oxidation layer.

12. The method of claim 7, wherein the solid material is a dielectric layer.

13. The method of claim 7, wherein the solid material is formed using an atomic layer deposition process or a chemical vapor deposition process.

14. The method of claim 7, wherein forming the solid material comprises:
introducing the reactant onto the substrate;
chemisorbing a first portion of the reactant on the substrate and physisorbing a second portion of the reactant on the substrate;
introducing the oxidizing agent onto the substrate; and
reacting the first portion of the reactant with the oxidizing agent.

15. The method of claim 14, wherein the steps of forming the solid material is repeated at least once.

16. The method of claim 14, further comprising:
removing the second portion of the reactant; and
removing the portion of the oxidizing agent that has not reacted with the first portion of the reactant.

17. The method of claim 7, wherein the ratio between the first organometallic compound and the second organometallic compound is in a range from about 1:0.5 to about 1:5.

18. The method of claim 7, wherein the method is carried out in an environment having a temperature in a range of about 250° C. to about 500° C.

19. The method of claim 7, wherein the method is carried out in an environment having a pressure in a range of about 0.01 Torr to about 10 Torr.

* * * * *